(12) United States Patent
Knoepfle et al.

(10) Patent No.: US 11,259,853 B2
(45) Date of Patent: *Mar. 1, 2022

(54) IMPLANT FOR BONE FIXATION (71) Applicant: Stryker European Operations Holdings LLC, Kalamazoo, MI (US)

(72) Inventors: Christian Knoepfle, Donaueschingen (DE); Karl Greiner, Muehlheim (DE); Manfred Schmuck, Muehlheim (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 148 days.

This patent is subject to a terminal disclaimer.

(21) Appl. No.: 16/374,942

(22) Filed: Apr. 4, 2019

(65) Prior Publication Data

US 2019/0223928 A1 Jul. 25, 2019

Related U.S. Application Data

(63) Continuation of application No. 14/991,181, filed on Jan. 8, 2016, now Pat. No. 10,292,742.

(30) Foreign Application Priority Data

Jan. 9, 2015 (EP) .................................. 15000033

(51) Int. Cl.
*A61B 17/82* (2006.01)
*A61B 17/80* (2006.01)
(Continued)

(52) U.S. Cl.
CPC .......... *A61B 17/82* (2013.01); *A61B 17/8076* (2013.01); *A61B 17/823* (2013.01);
(Continued)

(58) Field of Classification Search
CPC ....... A61B 17/82; A61B 17/823; A61B 17/80; A61B 17/8076
See application file for complete search history.

(56) References Cited

U.S. PATENT DOCUMENTS 1,616,232 A 2/1927 Roberts et al.
3,926,193 A 12/1975 Hasson
(Continued)

FOREIGN PATENT DOCUMENTS

CA 2286111 A1 10/1998
CA 2439094 A1 9/2002
(Continued)

OTHER PUBLICATIONS

"Non-Toxic and Bio-Compatible Type 2 Titanium Anodizing", 2003, XP055117504, Retrieved from the Internet: <URL: http://www.danco.net/PDF-DOWNLOADS/TITANIUM II. pdf>, [retrieved on May 12, 2014].
(Continued)

*Primary Examiner* — Christopher J Beccia
(74) *Attorney, Agent, or Firm* — Lerner, David, Littenberg, Krumholz & Mentlik, LLP (57) ABSTRACT

An implant for bone fixation is presented. The implant comprises an elongated member configured to be wound around bone parts that are to be fixed. Further, an engagement feature is provided that is coupled to the elongated member and configured to engage a portion of the elongated member so as to secure the implant in a loop around the bone parts. A fastening member is arranged between and coupled to the elongated member and the engagement member. The fastening member comprises at least one opening for receiving a bone fastener. In one variant, at least one visual indicator indicating a region of the fastening member to be severed in order to detach the implant is provided. In another variant, at least one of the engagement member and the
(Continued)

elongated member are coupled to the fastening member by injection molding.

20 Claims, 8 Drawing Sheets

(51) Int. Cl.
 *A61B 17/00* (2006.01)
 *A61B 17/86* (2006.01)
 *A61B 90/00* (2016.01)
(52) U.S. Cl.
 CPC ....... *A61B 17/8052* (2013.01); *A61B 17/8085* (2013.01); *A61B 17/86* (2013.01); *A61B 2017/00407* (2013.01); *A61B 2017/00526* (2013.01); *A61B 2017/00955* (2013.01); *A61B 2090/037* (2016.02)

(56) References Cited

U.S. PATENT DOCUMENTS

| | | | |
|---|---|---|---|
| 4,119,091 A | 10/1978 | Partridge | |
| 4,201,215 A | 5/1980 | Crossett et al. | |
| 4,279,248 A | 7/1981 | Gabbay | |
| 4,512,346 A | 4/1985 | Lemole | |
| 4,535,764 A | 8/1985 | Ebert | |
| 4,583,541 A | 4/1986 | Barry | |
| 4,802,477 A | 2/1989 | Gabbay | |
| 4,944,753 A | 7/1990 | Burgess et al. | |
| 5,047,034 A | 9/1991 | Sohngen | |
| 5,053,212 A | 10/1991 | Constantz et al. | |
| 5,139,498 A | 8/1992 | Astudillo Ley | |
| 5,146,654 A | 9/1992 | Caveney et al. | |
| 5,164,187 A | 11/1992 | Constantz et al. | |
| 5,188,670 A | 2/1993 | Constantz | |
| 5,279,831 A | 1/1994 | Constantz et al. | |
| 5,417,698 A | 5/1995 | Green et al. | |
| 5,549,619 A | 8/1996 | Peters et al. | |
| 5,653,711 A | 8/1997 | Hayano et al. | |
| 5,827,286 A | 10/1998 | Incavo et al. | |
| 5,941,881 A | 8/1999 | Barnes | |
| 5,964,763 A | 10/1999 | Incavo et al. | |
| 5,964,932 A | 10/1999 | Ison et al. | |
| 5,968,253 A | 10/1999 | Poser et al. | |
| 6,007,538 A | 12/1999 | Levin | |
| 6,051,007 A | 4/2000 | Hogendijk et al. | |
| 6,053,970 A | 4/2000 | Ison et al. | |
| 6,093,201 A | 7/2000 | Cooper et al. | |
| 6,200,318 B1 | 3/2001 | Har-Shai et al. | |
| 6,217,580 B1 | 4/2001 | Levin | |
| 6,302,899 B1 | 10/2001 | Johnson et al. | |
| 6,540,769 B1 | 4/2003 | Miller, III | |
| 6,558,709 B2 | 5/2003 | Higham | |
| 6,596,338 B2 | 7/2003 | Scott et al. | |
| 6,821,528 B2 | 11/2004 | Scott et al. | |
| 6,872,210 B2 | 3/2005 | Hearn | |
| 6,969,398 B2 | 11/2005 | Stevens et al. | |
| 7,033,377 B2 | 4/2006 | Miller, III | |
| 7,635,364 B2 | 12/2009 | Barrall et al. | |
| 7,695,473 B2 | 4/2010 | Ralph et al. | |
| 7,740,649 B2 | 6/2010 | Mosca et al. | |
| 7,871,411 B2 | 1/2011 | Grevious | |
| 8,221,421 B2 | 7/2012 | Hearn | |
| 8,460,295 B2 | 6/2013 | McClellan et al. | |
| 8,486,114 B2 | 7/2013 | Gillard et al. | |
| 9,358,054 B2 | 6/2016 | Garcia et al. | |
| 9,474,553 B2 | 10/2016 | Koch | |
| 10,292,742 B2 * | 5/2019 | Knoepfle | A61B 17/823 |
| 10,433,889 B2 | 10/2019 | Knoepfle | |
| 2002/0077659 A1 | 6/2002 | Johnson et al. | |
| 2002/0128654 A1 * | 9/2002 | Steger | A61B 17/8076 606/291 |
| 2002/0143336 A1 | 10/2002 | Hearn | |
| 2003/0049324 A1 | 3/2003 | Vogt et al. | |
| 2003/0077381 A1 | 4/2003 | Scott et al. | |
| 2003/0083694 A1 | 5/2003 | Miller | |
| 2003/0212399 A1 | 11/2003 | Dinh et al. | |
| 2004/0010256 A1 | 1/2004 | Gabbay | |
| 2004/0133206 A1 | 7/2004 | Stevens et al. | |
| 2005/0070928 A1 | 3/2005 | Heino et al. | |
| 2005/0124996 A1 | 6/2005 | Hearn | |
| 2005/0267475 A1 | 12/2005 | Miller | |
| 2005/0288674 A1 | 12/2005 | Golobek | |
| 2006/0116683 A1 | 6/2006 | Barrall et al. | |
| 2006/0122611 A1 | 6/2006 | Morales et al. | |
| 2006/0134160 A1 | 6/2006 | Troczynski et al. | |
| 2006/0161161 A1 | 7/2006 | Shifrin et al. | |
| 2006/0195101 A1 | 8/2006 | Stevens | |
| 2006/0259141 A1 | 11/2006 | Roman et al. | |
| 2006/0276794 A1 | 12/2006 | Stern | |
| 2007/0038218 A1 | 2/2007 | Grevious | |
| 2007/0043371 A1 | 2/2007 | Teague et al. | |
| 2007/0213832 A1 | 9/2007 | Wen | |
| 2007/0259101 A1 | 11/2007 | Kleiner et al. | |
| 2008/0154312 A1 | 6/2008 | Colleran et al. | |
| 2008/0221578 A1 | 9/2008 | Zeitani | |
| 2008/0306579 A1 | 12/2008 | Dolan et al. | |
| 2009/0118774 A1 | 5/2009 | Miller, III | |
| 2009/0118775 A1 | 5/2009 | Burke | |
| 2009/0138054 A1 | 5/2009 | Teague et al. | |
| 2009/0234357 A1 | 9/2009 | Morales et al. | |
| 2009/0234358 A1 | 9/2009 | Morales et al. | |
| 2009/0248091 A1 | 10/2009 | Teague et al. | |
| 2009/0269480 A1 | 10/2009 | Berglund | |
| 2010/0094294 A1 | 4/2010 | Gillard et al. | |
| 2010/0179600 A1 | 7/2010 | Steger et al. | |
| 2010/0305569 A1 | 12/2010 | Leuenberger et al. | |
| 2010/0318085 A1 | 12/2010 | Austin et al. | |
| 2011/0015681 A1 * | 1/2011 | Elsbury | A61B 17/8057 606/286 |
| 2011/0125193 A1 | 5/2011 | Grevious | |
| 2011/0166612 A1 | 7/2011 | Bardaji Pascual et al. | |
| 2011/0295257 A1 | 12/2011 | McClellan et al. | |
| 2011/0313474 A1 | 12/2011 | Gabele | |
| 2013/0261625 A1 * | 10/2013 | Koch | A61B 17/1604 606/74 |
| 2013/0338719 A1 | 12/2013 | Madjarov | |
| 2014/0100573 A1 | 4/2014 | Llas Vargas et al. | |
| 2014/0142638 A1 | 5/2014 | Goodwin et al. | |
| 2015/0045794 A1 * | 2/2015 | Garcia | A61B 17/8076 606/74 |

FOREIGN PATENT DOCUMENTS

| | | |
|---|---|---|
| CN | 101537208 A | 9/2009 |
| CN | 202235628 U | 5/2012 |
| DE | 202004021763 U1 | 9/2010 |
| DE | 102010021737 A1 | 11/2011 |
| DE | 102011109677 A1 | 2/2013 |
| EP | 0238219 A1 | 9/1987 |
| EP | 0597259 A2 | 5/1994 |
| EP | 0608592 A1 | 8/1994 |
| EP | 0806212 A1 | 11/1997 |
| EP | 0608592 B1 | 8/1998 |
| EP | 1099416 A2 | 5/2001 |
| EP | 1121058 A1 | 8/2001 |
| EP | 1521552 A1 | 4/2005 |
| EP | 1365693 B1 | 1/2006 |
| EP | 1429674 B1 | 3/2006 |
| EP | 1654994 A1 | 5/2006 |
| EP | 1691702 A1 | 8/2006 |
| EP | 1732460 B1 | 5/2010 |
| EP | 1885268 B1 | 7/2010 |
| EP | 2063799 B1 | 9/2010 |
| EP | 2367489 A1 | 9/2011 |
| EP | 1748738 B1 | 10/2011 |
| EP | 3042622 A1 | 7/2016 |
| WO | 9004366 A1 | 5/1990 |
| WO | 9505782 A1 | 3/1995 |
| WO | 9844850 A1 | 10/1998 |
| WO | 0022992 A1 | 4/2000 |
| WO | 02/067795 A1 | 9/2002 |
| WO | 03037201 A1 | 5/2003 |

(56) References Cited

FOREIGN PATENT DOCUMENTS

| | | |
|---|---|---|
| WO | 2004006784 A1 | 1/2004 |
| WO | 2004078218 A2 | 9/2004 |
| WO | 2005055844 A1 | 6/2005 |
| WO | 2005117726 A2 | 12/2005 |
| WO | 2006135935 A1 | 12/2006 |
| WO | 2007084238 A2 | 7/2007 |
| WO | 2008034537 A1 | 3/2008 |
| WO | 2009100792 A2 | 8/2009 |
| WO | 2010024946 A1 | 3/2010 |
| WO | 2010042946 A1 | 4/2010 |
| WO | 2010126436 A1 | 11/2010 |
| WO | 2011153676 A1 | 12/2011 |
| WO | 2013013218 A2 | 1/2013 |
| WO | 2013067049 A1 | 5/2013 |
| WO | 2013072576 A1 | 5/2013 |
| WO | 2014081574 A1 | 5/2014 |
| WO | 2014144479 A1 | 9/2014 |
| WO | 2015142588 A2 | 9/2015 |

OTHER PUBLICATIONS

Aberg et al, Bisphosphonate incorporation in surgical implant coatings by fast loading and co-precipitation at low drug concentrations, J Mater Sci: Mater Med (2009) 20:2053-2061.

Abtahl et al, A bisphosphonate-coating improves the fixation of metal implants in human bone, A randomized trial of dental implants, Bone 50 (2012) 1148-1151.

Brohede et al, Multifunctional implant coatings providing possibilities for fast antibiotics loading with subsequent slow release, J Mater Sci: Mater Med (2009) 20:1859-1867.

Brunski et al, Biomaterials and Biomechanics of Oral and Maxillofacial Implants: Current Status and Future Developments, The Inrternational Journal of Oral & Maxillofacial Implants, 2000. 15-46.

European Search Report for EP 13003896.1 dated Jul. 17, 2014.

Extended European Search Report for Application No. 15000033.9 dated Jun. 24, 2015.

F. Chai et al, Antibacterial activation of hydroxyapatite (HA) with controlled porosity by different antibiotics, Biomolecular Engineering 24 (2007) 510-514.

Forsgren et al, Co-loading of bisphosphonates and antibiotics to a biomimetic hydroxyapatite coating, Biotechnol Lett (2011) 33 :1265-1268.

Hetrick et al, Reducing implant-related infections: active release strategies, I Chern. Soc. Rev., 2006, 35, 780-789.

Hutson et al, Infections in Periarticular Fractures of the Lower Extremity Treated with Tensioned Wire Hybrid Fixators, Journal of Orthopaedic Trauma vol. 12, No. 3, 1998, pp. 214-218.

International Preliminary Report on Patentability Chapter II, for Application No. PCT/EP2013/066408 dated Sep. 25, 2015.

International Search Report and Written Opinion for Application No. PCT/EP2013/066408 dated Oct. 22, 2013.

International Search Report for Application No. PCT/EP2013/068082 dated May 26, 2014.

International Search Report for Application No. PCT/IB2014/060905 dated Jun. 26, 2014.

International Search Report for Application No. PCT/IB2014/062454 dated Sep. 29, 2014.

James M Anderson, Biological Responses to Materials, Annu. Rev. Mater. Res. 2001. 31:81-110.

Johan Forsgren et al, Formation and adhesion of biomimetic hydroxyapatite deposited on titanium substrates, Acta Biomaterialia 3 (2007) 980-984.

K.C. Baker et al, Growth, characterization and biocompatibility of bone-like calcium phosphate layers biomimetically deposited on metallic substrata, Materials Science and Engineering C 26 (2006) 1351-1360.

Lilja et al, Photocatalytic and antimicrobial properties of surgical implant coatings of titanium dioxide deposited though cathodic arc evaporation, Biotechnol Lett (2012) 34:2299-2305.

Liu et al, Water-based sol-gel synthesis ofhydroxyapatite: process development, Biomaterials 22 (2001) 1721-1730.

M.P. Ginebra et al, Calcium phosphate cements as bone drug delivery systems: A review, Journal of Controlled Release 113 (2006) 102-110.

Ma et al, Electrophoretic deposition of porous hydroxyapatite scaffold, Biomaterials 24 (2003) 3505-3510.

Mahan et al, Factors in Pin Tract Infections, Department of Orthopedic Surgery, University of Louisville, Louisville, Ky., Mar. 1991 vol. 14 No. 3 V , pp. 305-308.

Masse et al, Prevention of Pin Track Infection in External Fixation with Silver Coated Pins: Clinical and Microbiological Results, J Biomed Mater Res (Appl Biomater) 53: 600-604, 2000.

Poelstra et al, Prophylactic treatment of gram-positive and gram-negative abdominal implant infections using locally delivered polyclonal antibodies, pp. 206-215.

Sergio Allegrini Jr., et al, Hydroxyapatite grafting promotes new bone formation and osseointegration of smooth titanium implants, Ann Anat 188 (2006) 143-151.

Stigter M et al: "Incorporation of different antibiotics into carbonated hydroxyapatite coatings on titanium implants. release and antibiotic efficacy", Journal of Controlled Release, Elsevier, Amsterdam, NL, vol. 99, No. 1, Sep. 14, 2004 (Sep. 14, 2004). pp. 127-137, XP004549075.

Stigter M et al: "Incorporation of tobramycin into biomimetic hydroxyapatite coating on titanium", Biomaterials. Elsevier Science Publishers BV, Barking, GB, vol. 23, No. 20, Oct. 1, 2002 (Oct. 1, 2002), pp. 4143-4153. XP004370405.

Synthes CMF, "Modular Sternal Cable System", 2006, 12 pages.

Synthes CMF, "Sternal ZipFix System—For fast and stable fixation of the sternum", Technique Guide, 2011, 26 pages.

Sörensen et al., "Biomechanical and antibacterial properties of Tobramycin loaded hydroxyapatite coated fixation pins", Journal of Biomedical Materials Research B: Applied Biomaterials, 2014, vol. 00B, Issue 00, 12 pages.

Sörensen et al., "Biomimetic Hydroxyapatite Coated Titanium Screws Demonstrate Rapid Implant Stabilization and Safe Removal In-Vivo", Journal of Biomaterials and Nanobiotechnology, 2015, 6, 20-35.

Tengvalla et al, Surface immobilized bisphosphonate improves stainless-steel screw fixation in rats, Biomaterials 25 (2004) 2133-2138.

Ulrika Brohede et al: "Multifunctional implant coatings providing possibilities for fast antibiotics loading with subsequent slow release", Journal of Materials Science: Materials in Medicine, Kluwer Academic Publishers, BO, vol. 20, No. 9, 28 Apr. 1, 2009 (Apr. 28, 2009) pp. 1859-1867, XP019730963.

Zilberman et al, Antibiotic-eluting medical devices for various applications, journal of Controlled Release 130 (2008) 202-215.

European Search Report for Application No. EP16002390.9 dated Mar. 31, 2017.

\* cited by examiner

IMPLANT FOR BONE FIXATION

CROSS-REFERENCE TO RELATED APPLICATION

This application is a continuation of U.S. application Ser. No. 14/991,181, filed on Jan. 8, 2016, which claims priority from European Patent Application No. 15 000 033.9, filed Jan. 9, 2015, the disclosures of which are each incorporated herein by reference.

TECHNICAL FIELD

The present disclosure generally relates to bone fixation. Specifically, the disclosure relates to an implant for fixing bone parts, to systems comprising the implant, and to methods of manufacturing the implant.

BACKGROUND OF THE INVENTION

Various surgical procedures require the surgeon to access the thoracic region of a patient. A known approach to access the thoracic region is to cut the sternum in two parts and separate these two parts from each other for gaining access to the thoracic region. After completion of the surgical procedure, the separated parts of the sternum are brought back to their initial positions and fixed, for example, with a bone plate attached to the sternum parts or a wire tensioned around the circumference of the sternum.

U.S. Pat. No. 5,417,698 discloses a closure element to be looped around a human sternum. The closure element comprises a strap which is inserted through and retained by a tightening plate.

U.S. Pat. No. 8,460,295 discloses a sternum repair device including a central body and a plurality of bands extending from the central body. The bands are wrapped around the sternum to keep the sternum parts together. The central body includes a view window which is used by a surgeon to line up the device during installation on the sternum.

U.S. Pat. No. 8,486,114 discloses a cerclage system including a cable that encircles the sternum parts and a bone plate having channels to receive segments of the cable. The bone plate further includes a pair of locking studs to lock the cable within the channels to the bone plate.

EP 0 608 592 B1 discloses an assembly for banding a sternum. The assembly comprises an elongated flexible band, a needle at one end of the band and a buckle proximate the other end of the band. A main section of the band includes a plurality of spaced apart slots which can engage at a locking mechanism.

After the thoracic procedure such as, for example, a bypass operation has been carried out on a patient and the sternum parts have been fixed using a suitable fixation assembly, the patient is normally kept under surveillance. If it is detected that the surgical procedure has failed or that complications occur, it may be desirable for the surgeon to again open the fixation system for accessing the thoracic region. The time required for this opening procedure may be critical for the patient's health and even life.

In other situations, a cable or wire tensioned around the sternum parts (so-called "primary closure") might become loose or break due to the load applied to the thoracic region of the patient. In such cases, the sternum part fixation may need to be stabilized by, for example, a bone plate (so-called "secondary closure").

Similar or related problems occur in connection with other surgical procedure in which two or more bone parts need to be fixed.

There is a need for an implant for bone fixation that can be attached or separated fast, easily and at low risk for the patient. Furthermore, there is a need for such an implant which provides a high implant-bone-construct-stability. Moreover, there is generally a need for an implant for bone fixation that exhibits good surgical results.

SUMMARY OF THE INVENTION

According to a first aspect of the present invention an implant for bone fixation is provided. The implant comprises an elongated member, an engagement member, a fastening member, and at least one visual indicator. The elongated member is configured to be wound around bone parts that are to be fixed and the engagement member is coupled to the elongated member and configured to engage a portion of the elongated member so as to secure the implant in a loop around the bone parts. The fastening member is arranged between and coupled to the elongated member and the engagement member, the fastening member comprising at least one opening for receiving a bone fastener. The at least one visual indicator indicates a region of the fastening member to be severed in order to detach the implant.

In some implementations, at least the elongated member and the fastening member may be made of different materials. As an example, the elongated member may be made from a material that exhibits a certain flexibility so that the elongated member can be wound around the bone parts. On the other hand, the fastening member may be made from a rigid material that will not, or not easily, deform upon an engagement with the bone fastener. As such, the rigidity of the fastening member material may generally be higher than the rigidity of the engagement member material.

In a first realization, the region of the fastening member indicated by the visual indicator may be a region of reduced mechanical strength of the fastening member. As such, the mechanical strength of the fastening member may be lower in the region indicated by the visual indicator than in other regions of the fastening member. The mechanical strength may be defined in relation to a force required to sever (cut, saw, etc.) the fastening member. In another realization, that may be combined with the first realization, the region of the fastening member indicated by the visual indicator may be a region that is to be severed from a surgical viewpoint (e.g., so as to separate the bone parts).

The fastening member may be coupled to at least one of the elongated member and the engagement member by injection molding. In one variant, the fastening member comprises a first end and a second end opposite to the first end. The elongated member may be injection molded to the first end of the fastening member. Additionally, or as an alternative, the engagement member may be injection molded to the second end of the fastening member. As an example, the elongated member may be injection molded to the first end of the fastening member in a first injection molding process and the engagement member may be injection molded to the second end of the fastening member in a second injection molding process separate from the first injection molding process. The first and second injection molding processes may be performed at separate points in time (e.g., one after the other) or substantially at the same point in time (e.g., simultaneously).

If injection molding is used for manufacturing the implant, the visual indicator may be defined by a portion of the fastening member that remains exposed from injection molding. As an example, the exposed region may be located between the first end of the fastening member associated with the first injection molding process and the second end of the fastening member associated with the second injection molding process. The exposed region may have a width of 1 to 10 mm.

Regardless of the manufacturing process, the visual indicator may also be realized in any other manner. As an example, the visual indicator may be printed on the implant. Additionally, or in the alternative, the visual indicator may be realized as a three-dimensional structure, for example so as to comprise a notch or a groove. As will be appreciated, such a three-dimensional structure could also facilitate severing of the fastening member.

The visual indicator may in one variant extend in a direction substantially perpendicular to an extension of the elongated member. For example, the visual indicator may indicate a direction in which the fastening member is to be severed. In another variant, the visual indicator may have no preferred extension (e.g., it may take the form of a point, circle, or similar non-directed feature).

The fastening member may comprise a plurality of openings. In this regard, the fastening member may comprise at least a first opening and a second opening that are substantially aligned with an extension of the elongated member. The visual indicator may be located between the first opening and the second opening. In variants in which the fastening member comprises more than two openings, still a single visual indicator may be provided (e.g., separating the plurality of openings in two sets of two or more openings each).

In a fastening member with several openings, the first opening may be configured to be located proximate to a first bone portion and the second opening may configured to be located proximate to a second bone portion to be fixed. There may be further openings located proximate to the first and second bone portions, respectively (e.g., to insert two or more bone fasteners in each bone portion).

In a second aspect of the present invention, a further implant for bone fixation is provided. The implant comprises an elongated member configured to be wound around bone parts that are to be fixed, an engagement member coupled to the elongated member and configured to engage a portion of the elongated member so as to secure the implant in a loop around the bone parts, and a fastening member arranged between and coupled to the elongated member and the engagement member. The fastening member comprises at least one opening for receiving a bone fastener and is coupled to at least one of the elongated member and the engagement member by injection molding.

The implant of the second aspect may comprise a visual indicator as generally discussed herein. In other variants, no such visual indicator may be provided.

In all the implant aspects presented herein, the elongated member may comprise a plurality of engagement features provided along an extension of the elongated member. In such a case, the engagement member may be configured to be brought into selective engagement with one of the engagement features. In one variant, the engagement features and the engagement member realize a zip tie-type engagement mechanism.

In all the implant aspects, a hook member may be coupled to the elongated member at an end thereof opposite to the engagement member. The hook member may be coupled to the elongated member by injection molding or may form an integral part of the elongated member.

In all the implant aspects, the at least one opening of the fastening member may comprise a locking feature configured to lock the bone fastener to the fastening member. Further, the locking feature may be configured to engage the bone fastener at a selected angular orientation. The locking feature may take the form of a circumferential lip (e.g., of increased material thickness) or of a thread. The at least one opening of the fastening member may comprise a threaded portion on a bone facing side of the fastening member and an unthreaded portion on a side opposite to the bone facing side.

A portion of the fastening member adjacent to the at least one opening may have a conical, convex or spherical taper which substantially tapers inwardly in a direction toward a bone facing surface of the fastening member. Thus, the fastening member can be configured to exert a compression force when a bone fastener is screwed or inserted through the opening into a bone part.

In one implementation, the at least one opening of the fastening member may be adjacent to an inclined surface onto which a bone fastener is able to slide in a fastening or compression position. The inclined surface may permit a bone fastener to slide laterally or longitudinally with respect to the opening or the fastening member. Further, at least one opening of the fastening member may define a predetermined direction for a bone fastener. The inclined surface may have a predetermined angle with respect to an extension plane of the attachment member. The predetermined angle can be between about 20 and 70 degrees, for example about 40 to 50 degrees (e.g., about 45 degrees).

The at least one opening of the fastening member may generally be a circular or elongated hole. The elongated hole may be an oblong hole. Further, the elongated hole may extend substantially parallel with respect to a longitudinal direction of the fastening member or of the flexible elongated member. Alternatively, the elongated hole may extend substantially perpendicular to a longitudinal direction of the fastening member or of the elongated member.

The implant may have a larger width in a region of the one or more openings compared to a general width of the elongated member. The thickness of the fixation assembly may be larger in a region of the one or more openings compared to a general thickness of the elongated member.

In all the implant aspects, the fastening member may be made from a metallic material (e.g., stainless steel, titanium or a titanium alloy). In addition, or as an alternative, at least one of the elongated member and the engagement member may be made from a polymeric material (e.g., polyetheretherketone, PEEK). In certain variants, the engagement member and the fastening member may at least partially be realized as a one-piece structure. As such, the engagement member may at least partially be made from the same material than the fastening member.

Also provided is a an implant system comprising the implant presented herein and at least one bone fastener configured to be inserted through the at least one opening of the fastening member into bone.

As said, the at least one opening may comprise a first locking feature configured to lock the bone fastener to the fastening member. In such a case the bone fastener may comprise a second locking feature configured to engage the first locking feature. As an example, the first locking feature may take the form of a circumferential lip or thread. The second locking feature may take the form of a thread. This thread may be provided in a head region of the bone fastener or immediately below the head region. The second locking feature may be different from a bone engaging thread of the bone fastener.

Still further, a method of manufacturing an implant is provided, wherein the implant has an elongated member configured to be wound around bone parts that are to be fixed, an engagement member coupled to the elongated member and configured to engage a portion of the elongated member so as to secure the implant in a loop around the bone parts, and a fastening member arranged between and coupled to the elongated member and the engagement member, the fastening member comprising at least one opening for receiving a bone fastener. The method comprises coupling the fastening member to at least one of the elongated member and the engagement member by injection molding.

The method aspect may comprise one or more further steps or substeps to manufacture the implant presented herein.

BRIEF DESCRIPTION OF THE DRAWINGS

The above and other features, aspects and advantages of the present disclosure will now be explained with reference to the following description of exemplary embodiments and the accompanying drawings, wherein.

DETAILED DESCRIPTION

In the following description, exemplary embodiments of a bone fixation implant and an implant system comprising the implant and a bone fastener will be explained with reference to the drawings. The same reference numerals will be used to denote the same or similar structural features.

Figure 1:
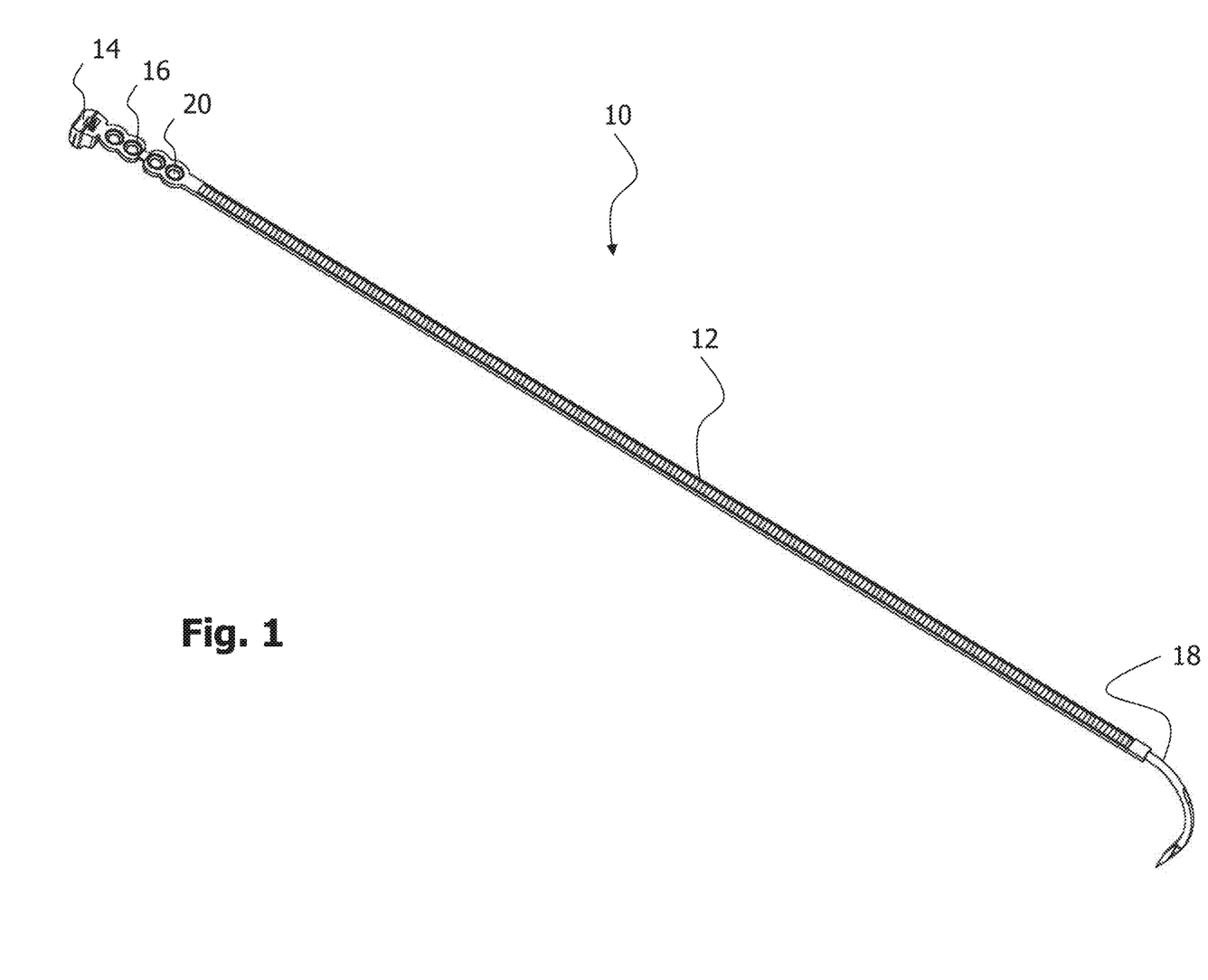
FIG. 1 is a perspective view of an embodiment of an implant for bone fixation.

FIG. 1 shows a perspective view of an embodiment of a bone fixation implant 10. In the embodiment shown in FIG. 1, the implant 10 is configured and dimensioned for fixing bone parts of a sternum. It will be appreciated that the present disclosure is not limited to this surgical indication. Rather, the present disclosure can also be applied in connection with fixing bone parts in other regions of the human anatomy, possibly with suitably adapted configurations and dimensions.

The implant 10 shown in FIG. 1 comprises an elongated member 12, an engagement member 14 coupled to the elongated member 12, and a fastening member 16 arranged between and coupled to the elongated member 12 and the engagement member 14.

The elongated member 12 is configured to be wound around the sternum parts that are to be fixed. As such, the elongated member 12 is made from a generally flexible material and has a suitable length of approximately 10 to 35 cm. The engagement member 14 is configured to engage a portion of the elongated member 12 so as to secure the implant 10 in a loop around the sternum parts. Details of how the engagement member 14 engages the elongated member 12 will be described in more detail below.

As also shown in FIG. 1, the implant 10 further comprises a hook member 18 coupled to the elongated member 12 at an end thereof opposite to the engagement member 14. The hook member 18 is configured to facilitate threading of the elongated member 12 around the sternum parts that are to be fixed. It will be appreciated that depending on the surgical indication, the hook member 18 could also be omitted or substituted by another member (e.g., a linear needle) to support a proper placement of the elongated member 12 by a surgeon.

In the following, the configuration of the implant portion comprising the engagement member 14 and the fastening member 16 will be described in more detail with reference to FIGS. 2 and 3. As illustrated therein, the fastening member 16 comprises a plurality of openings 20. Each opening 20 is configured to receive a bone fastener such as a bone screw or a bone pin. The openings 20 are substantially aligned with an extension of the elongated member 12. In the exemplary case of openings 20 having a circular shape, the centers of the openings 20 lie on an axis that coincides with an axis of the elongated member 12 in a non-wound (i.e., planar) state.

The fastening member 16 of the present embodiment comprises four openings 20. It will be appreciated that more or less openings 20 could be provided in other embodiments depending on the surgical needs.

Figure 2:
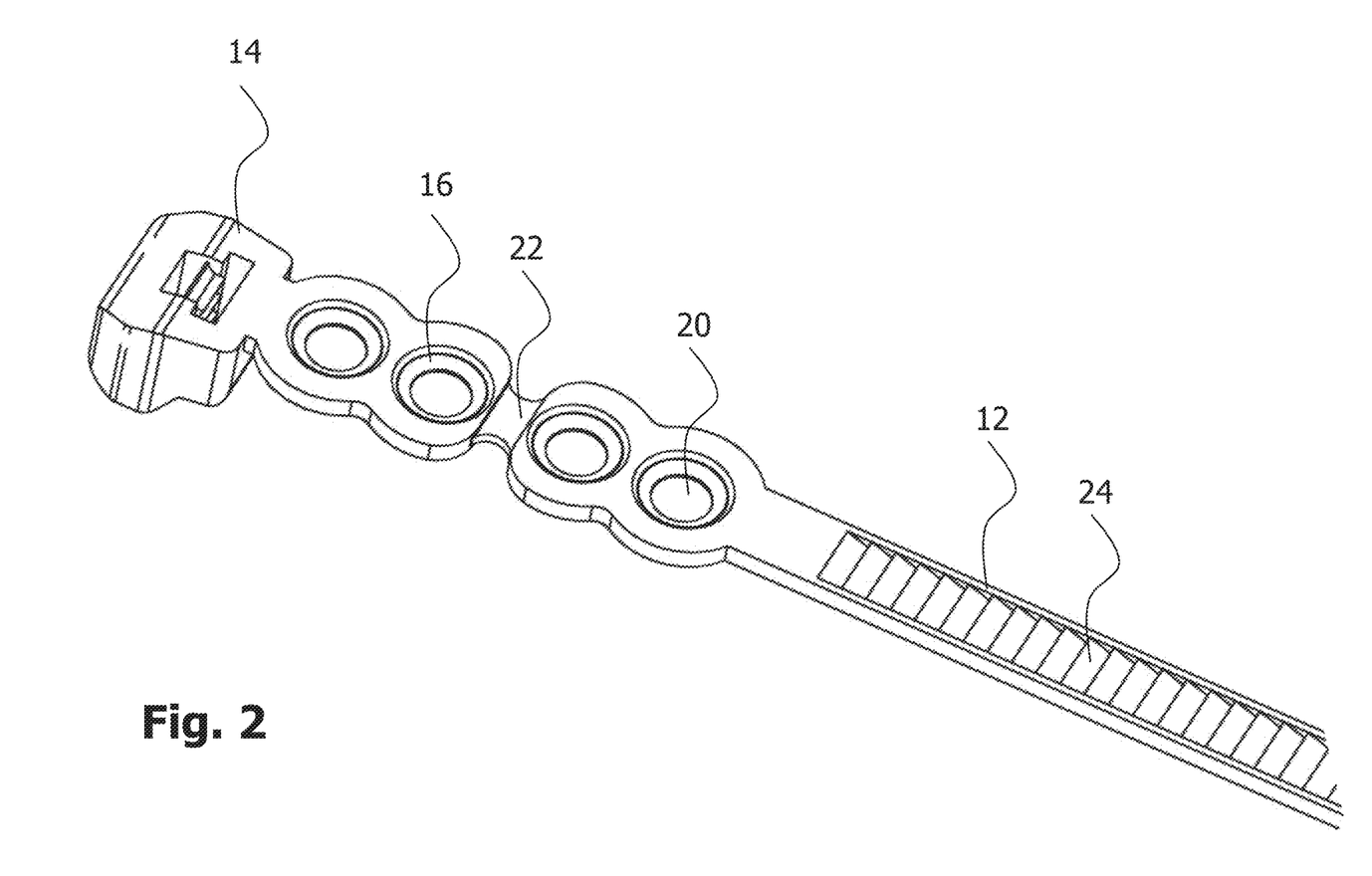
FIG. 2 is an enlarged perspective view of a portion of the implant of FIG. 1.
Figure 3:
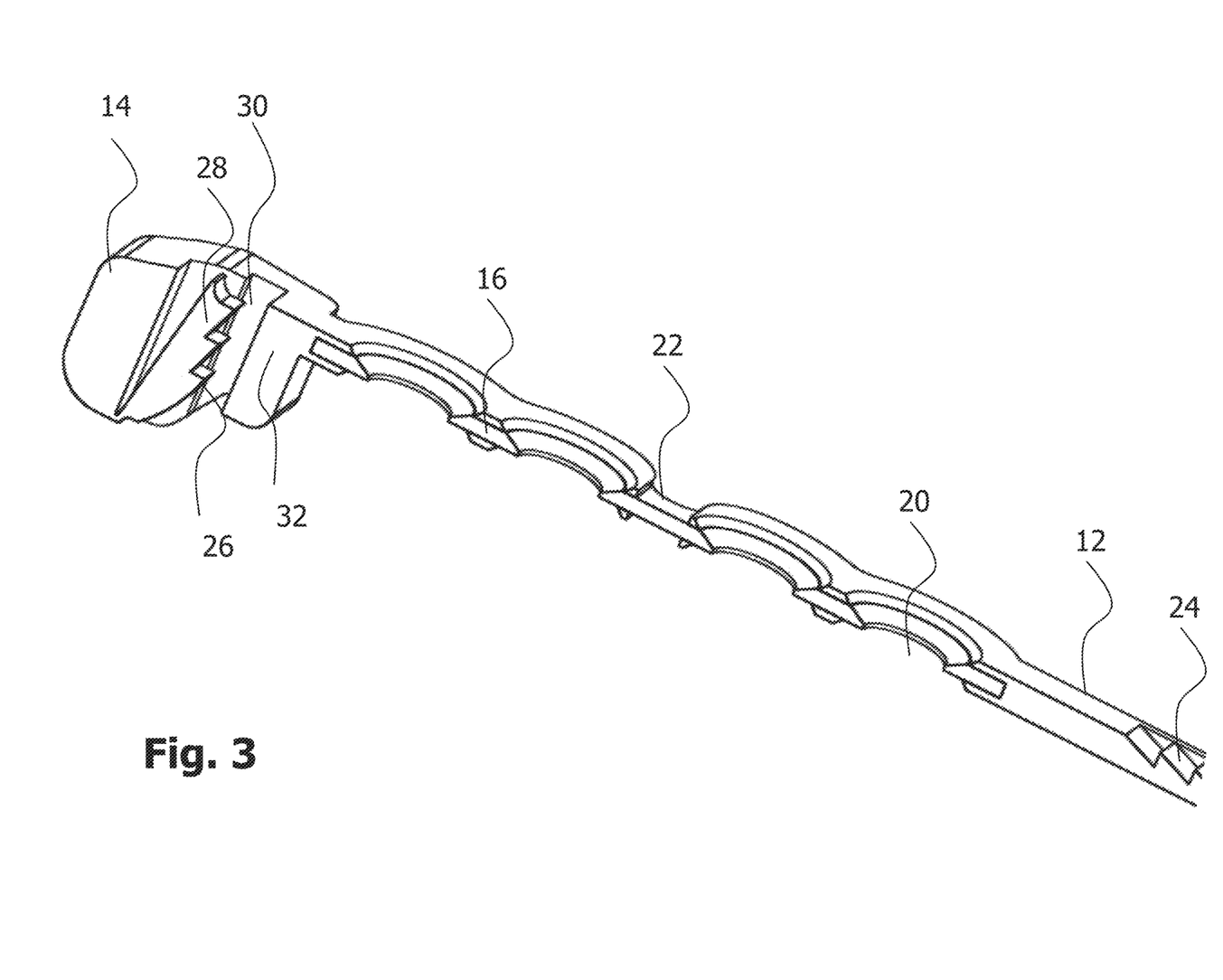
FIG. 3 is a perspective cross-sectional view of the implant portion shown in FIG. 2.

As illustrated in FIGS. 2 and 3, the four openings 20 are divided by a visual indicator 22 into two sets of two openings 20 each. The visual indicator 22 indicates a region of the fastening member 16 to be severed in order to detach the implant 10 after implantation. In the present embodiment, the visual indicator 22 has a generally rectangular shape with a larger extension that extends in a direction substantially perpendicular to the extension of the elongated member 12. The visual indicator 22 thus indicates the direction in which the fastening member 16 is to be severed.

The visual indicator 22 in the present embodiment marks a region of reduced mechanical strength of the fastening member 16 (explained in more detail below with reference to FIG. 4). As such, the visual indicator 22 indicates the region of the fastening member 16 that is easiest to sever by a surgical cutter in order to detach the implant 10.

In the context of fixing two sternum parts, the visual indicator 22 of the implant 10 after implantation will generally lie on a line along which the two sternum parts have been joined. That joining line will generally extend perpendicular to the extension of the fastening member 16. For this reason the visual indicator 22 separates a first set of two openings 20 that will be located proximate to one sternum portion from another set of two openings 16 that will be located proximate to the other sternum portion. Severing the fastening member in the region of the visual indicator 22 will therefore permit to separate the two sternum parts (e.g., in the case of medical complications) even when the bone fasteners attached via the openings 20 to the sternum parts remain in place.

It will be evident that severing the fastening member 16 in the region of the visual indicator 22 in order to detach the implant 10 provides a much quicker access to the thoracic region than detaching the implant 10 by removing multiple bone fasteners inserted to the openings 20 into the sternum parts. It should be noted that after severing the fastening member 16 it may still be required to also sever the elongated member 12 or another portion of the implant 10 to fully separate the sternum parts. In any case, the visual indicator 22 guides the surgeon towards the optimal fastening member region to be severed in order to quickly detach the implant 10.

The visual indicator 22 may generally be provided in many different ways, for example by printing it on the implant 10 (e.g., directly on the fastening member 10), by stamping a line or any other three-dimensional pattern in the implant 10 (e.g., directly in the fastening member 16), or in other ways. In the present embodiment, the visual indicator 22 is realized during the manufacturing process of the implant 10 by exposing a portion of the fastening member 16 during an injection molding process.

Specifically, as illustrated in FIG. 3, the fastening member 16 is coupled to the elongated member 12 and the engagement member 14 by injection molding. In this regard, the elongated member 12 is injection molded to a first end of the fastening member 16, while the engagement member 14 is injection molded to an opposite end of the fastening member 16. The visual indicator 22 is thus defined by a central portion of the fastening member 16 that remains exposed from injection molding.

In certain variants, the elongated member 12 is injection molded to the fastening member 16 in a first injection molding process and the engagement member 14 is injection molded to the fastening member 16 in a second injection molding process separate from the first injection molding process. The two injection molding processes may be performed essentially at the same point in time or at spaced apart points in time. It will further be appreciated that in certain embodiments the visual indicator 22 may be omitted. In such a case, or in other cases, the fastening member 16 may be injection molded to the elongated member 12 and to the engagement member 14 in a single injection molding process.

As will be appreciated, the fastening function of the fastening member 16 can best be fulfilled in case the fastening member 26 is made from a rigid material, such as metal (e.g., stainless steel, titanium, or a titanium alloy), especially if compression forces are to be applied via the bone fasteners inserted through the openings 20. On the other hand, the elongated member 12 will be manufactured from an at least partially flexible material since it needs to be wound around the bone parts that are to be fixed. As such, the elongated member can be made from a polymeric material such as PEEK.

The engagement member 14 may be made from the same material as the elongated member 12 or from a different material. As an example, the engagement member 14 may also be made from PEEK. In another variant, the engagement member 14 may at least partially be made from the same material as the fastening member 16. As an example, the engagement member 14 and the fastening member 16 may at least partially be realized as a one-piece structure.

As will be appreciated, using a polymeric material for the elongated member 12 and the engagement member 14 facilitates injection molding of those two members 12, 14 to the fastening member 16. However, the present disclosure in relation to the visual indicator 22 is not limited to manufacturing the implant 10 using one or more injection molding processes. Moreover, the visual indicator 22 could also be realized in connection with an implant 10 that is realized as a one-piece structure (e.g., from a polymeric material and, optionally, in a single injection molding process).

FIGS. 2 and 3 also illustrate the engagement mechanism that allows the engagement member 14 to engage a portion of the elongated member 12 so as to secure the implant 10 in a loop around the sternum parts. In more detail, the elongated member 12 comprises a plurality of engagement features 24 that are provided along essentially the entire length of the elongated member 12 (see FIG. 1). As can best be seen in FIG. 3, each individual engagement feature 24 has a sawtooth-like cross-section with a first surface that extends generally perpendicular to a plane defined by the elongated member 12 in an un-wound state, and a second surface at an angle to that plane.

The engagement member 14 comprises complementary engagement features 26 with a sawtooth-like profile. As shown in FIG. 3, those complementary engagement features 26 are provided on a deflectable pawl 28. The pawl 28 is located within an opening 30 that extends through a head portion 32 of the engagement member 14. The opening 30 has an axis that is substantially parallel to a center axis of each of the openings 20 in the fastening member 16.

The deflectable pawl 28 is attached to the head portion 14 at a bone facing side of the head portion 32 and configured to engage the engagement features 24 of the elongated member 12 in a zip tie-like manner upon threading the elongated member 12 through the opening 30 in the head portion 32 of the engagement member 14. The zip tie-like configuration of the engagement mechanism permits to generate a compression force when the implant 10 is looped around the sternum parts. This compression force presses the sternum parts against each other and facilitates bone healing.

It will be appreciated that in other embodiments other engagement mechanisms could be used. As an example, the elongated member 12 and the engagement member 14 could each also take the form of a band or wire that can be brought into engagement via knot or a dedicated coupling feature.

In the following, the configuration of the fastening member 16 will be described in more detail with reference to FIGS. 4 and 5. As shown therein, the fastening member 16 generally takes the form of an elongated bone plate with an undulating outer profile.

Specifically, the undulations in the outer profile correspond to the location of the openings 20 in the fastening member 16. As can also be seen in FIG. 4, the central portion of the fastening member 16 (i.e., the region between a first set of two adjacent openings and a second set of two adjacent openings) has a reduced mechanical strength to facilitate severing of the fastening member 16. In more detail, the central portion of the fastening member 16 is the region of the fastening member 16 with the smallest width. As illustrated in FIGS. 2 and 3, that fastening member region with the smallest width corresponds to the location of the visual indicator 22.

Figure 4:
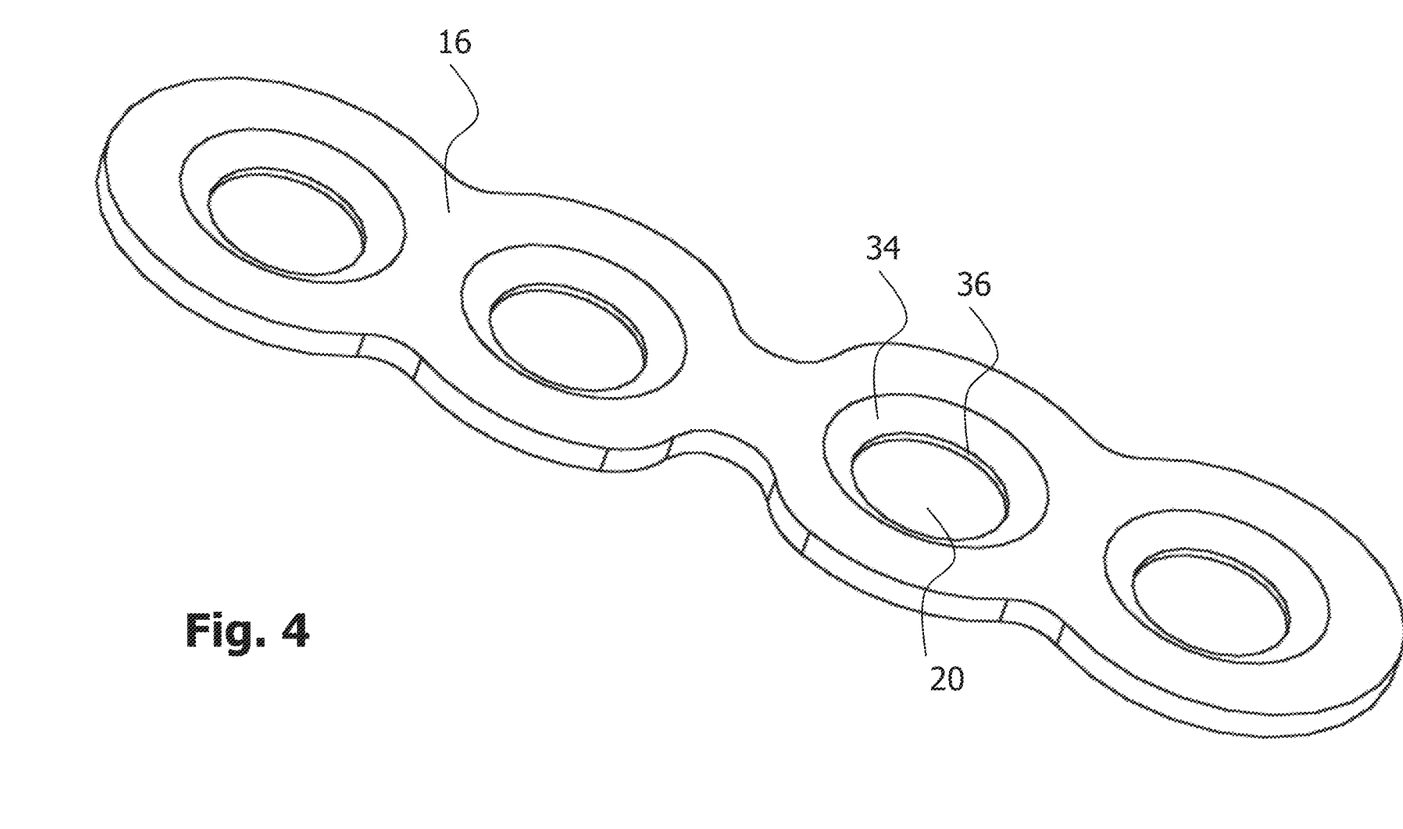
FIG. 4 is a perspective view of a fastening member for use in connection with the implant of FIG. 1.
Figure 5:
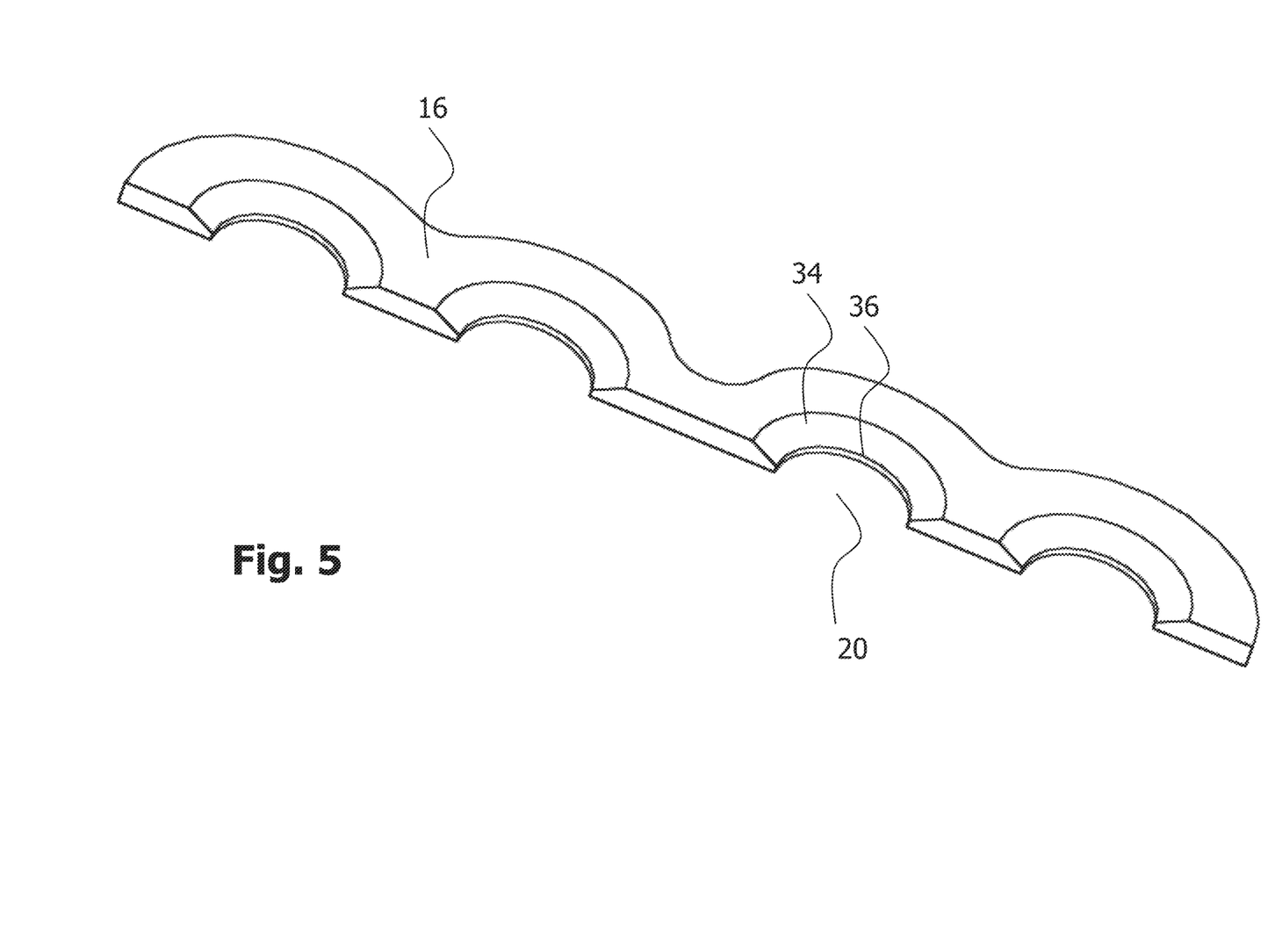
FIG. 5 is a perspective cross-sectional view of the fastening member shown in FIG. 4.

As also shown in FIGS. 4 and 5, the fastening member 16 comprises a conically tapering portion 34 towards each opening 20. In other embodiments, a spherical taper may be provided. The tapering portion 34 permits the generation of compression forces upon inserting a bone fastener through one of the openings 20. The compression forces result in the sternum parts being drawn towards the fastening member 16 so as to increase the implant-bone-construct-stability.

Further, each tapering portion 34 ends in a circumferential lip 36 of reduced material thickness around the respective hole 20. The lip 36 constitutes a locking feature configured to lock a bone fastener to the fastening member 16 as generally illustrated in FIG. 6 (for a different cross-sectional configuration of the fastening member 16).

Figure 6:
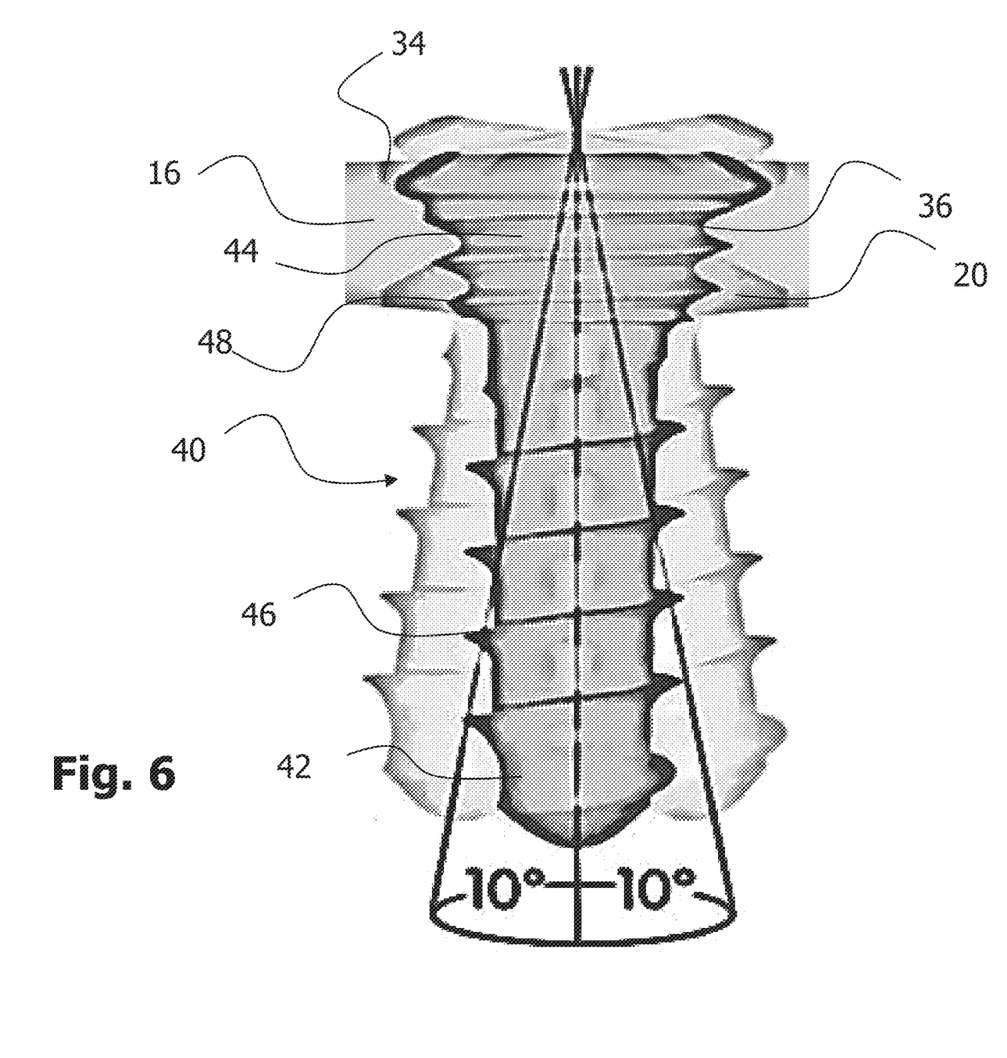
FIG. 6 is a schematic cross-sectional view illustrating an angular orientation of a bone fastener relative to a fastening member in accordance with a further embodiment.

FIG. 6 illustrates a bone screw 40 with a shaft 42 and a head 44. The shaft 42 of the bone screw 40 carries a bone thread 46 configured to engage bone. The head 44 of the bone screw 40 comprises a further thread 48 configured to engage the circumferential lip 36 at a selected angular orientation. As shown in FIG. 6, the selected angular orientation of the bone screw 40 may be within a range of 0° to 10° relative to the central axis of the opening 20. Upon screwing the bone screw 40 into bone, the thread 48 at the head portion 44 of the bone screw 40 will engage the circumferential lip 36 to lock the bone screw 40 at the selected angular orientation to the fastening member 14. As such, the thread 48 at the head 44 of the bone screw 40 constitutes a locking feature complementary to the circumferential lip 36 at the fastening member 16.

It will be appreciated that in other embodiments the circumferential lip 36 may be omitted or replaced by another locking feature, such as a thread. It will also be appreciated that in other embodiments the thread 48 provided at the head 44 of the bone screw 40 could also be omitted. In such a case the head 44 of the bone screw 40 could have a smooth and spherically or conically tapering configuration.

In the embodiment illustrated in FIG. 6, hole 20 tapers from a bone facing side of the fastening member 16 towards the lip 36 and also from the opposite side towards the circumferential lip 36. One or both of those tapers could be omitted.

Figure 7:
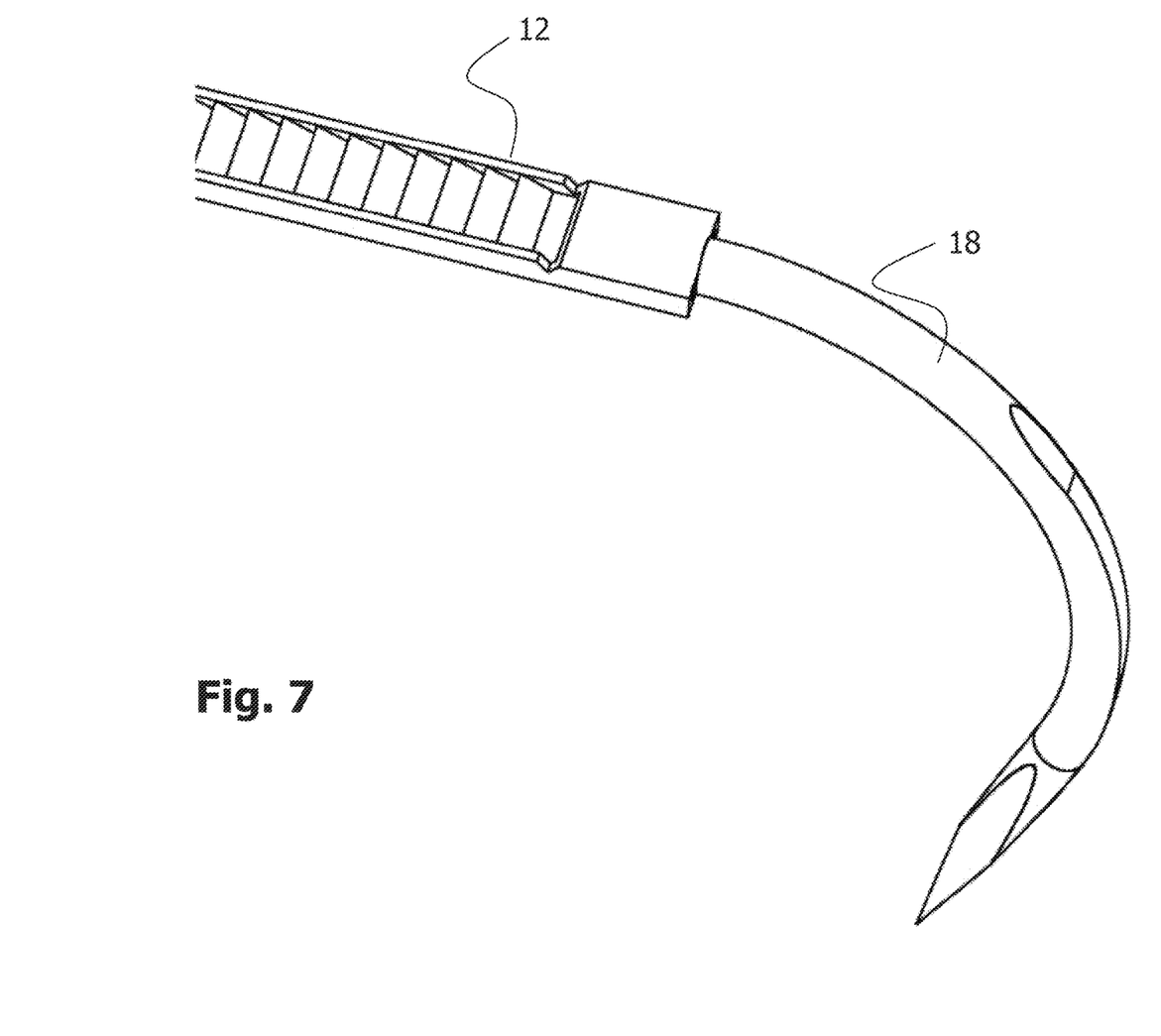
FIG. 7 is an enlarged perspective view of another portion of the implant of FIG. 1.
Figure 8:
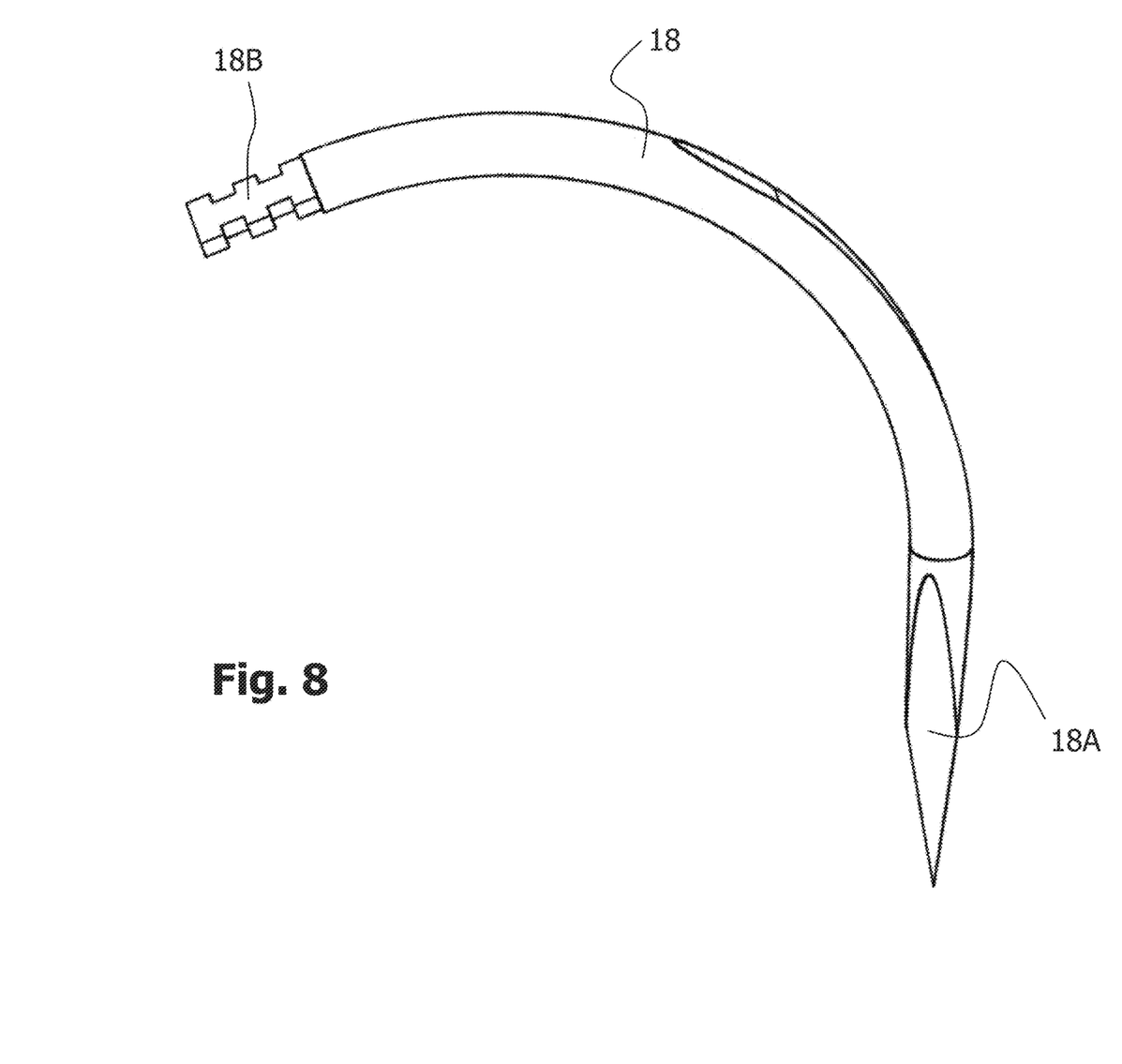
FIG. 8 is a perspective view of a hook member of the implant of FIG. 1.

Finally, FIGS. 7 and 8 illustrate the hook member 18 as well as the attachment of the hook member 18 to the elongated member 12. As shown in FIG. 8, the hook member 18 comprises a sharpened tip 18A at one end thereof as well as a structured region 18B at the opposite end. The structured region 18B facilitates injection molding of the elongated member 12 to the hook member 18, as generally illustrated in FIG. 7.

In the following, an exemplary method of using the implant 10 in connection with fixing two sternum parts will briefly be described. Similar methods may be applied in connection with other surgical indications for fixing bone parts in other regions of the human anatomy. In certain procedures, two sternum parts or portions may be separated by a bone cut. After these parts have been brought back together and preferably into their initial position with respect to one another, implant 10 is used for securing together these parts. U.S. Ser. No. 14/895,163 titled "Fixation Assembly with a Flexible Elongated Member for Fixing Parts of a Sternum," discloses in FIG. 10 thereof a fixation assembly attached to a sternum with bone parts having been brought back together and is hereby incorporated by reference herein in its entirety.

In a first step, the elongated member 12 is wound around the two sternum parts that are to be fixed. Winding the elongated member 12 around the sternum parts is facilitated by the hook member 18 with the sharpened tip 18A.

In a next step the hook member 18 and then the elongated member 12 are threaded through the opening 30 of the engagement member 14. In certain variants, the hook member 18 may be cut prior to that threading step, so that only the free end of the elongated member 12 (without the hook member 18) is threaded through the corresponding opening 30. Once the elongated member 12 enters the opening 30, the engagement features 24 on the elongated member 12 are engaged by the complementary engagement feature 26 on the pawl 29 in a zip tie-like manner (i.e., such that the elongated member 12 can only be tightened, but cannot become loose).

Then, the elongated member 12 is further drawn through the opening 30 so as to tighten the implant 10 around the two sternum parts. During that tightening process, the surgeon observes that the visual indicator 22 will substantially be placed on the joining line of the two sternum parts to enable a proper detachment. The tightening force is then increased further so as to compress the sternum parts together.

If only a primary closure is needed, the above steps may be repeated one or multiple times for one or more further implants 10. For primary closure, no further fixing of the implant 10 to the sternum parts using bone fasteners is needed.

On the other hand, in case of a need for secondary closure, one or two fixation members are inserted in each bone part through the respective openings 20. As has been explained above with reference to FIG. 6, each bone fasteners may be inserted at a selected angular orientation and may be locked to the implant 10 using the corresponding locking features 36, 48. The bone fasteners 40 may each have a self-drilling thread 46. Alternatively, pilot holes may be drilled through the openings 20 prior to insertion of the bone fasteners 40. In both cases, the thread 46 may be self-tapping.

If a surgeon requires quick access to the thoracic region after the implant 10 has been implanted using one or more bone fasteners 40, the surgeon uses a cutter to sever the fasting member 16 in the region of the visual indicator 22. In a further step, the surgeon cuts the elongated member 12 so the sternum parts can be separated from each other. The bone fasteners 40 may remain in place until after the thoracic region needs to be closed again via a primary or secondary closure process.

The features described in the above description and illustrated in the accompanying drawings can be modified, replaced or combined to result in different embodiments. It will thus be apparent that the present disclosure may be varied in many ways. Such variations are not to be regarded as a departure from the scope of the present disclosure, and they are intended to be included within the scope of the following claims.

The invention claimed is:

1. An implant for bone fixation, comprising:
an elongated member defining a first end and a second end, the elongated member configured to be wound around bone portions of a sternum of a patient that are to be fixed;
a fastening member coupled to the second end of the elongated member, the fastening member including at least one opening for receiving a bone fastener; and
an engagement member coupled to the fastening member and spaced apart from the second end of the elongated member, the engagement member configured to engage a portion of the elongated member located between the first and second ends so as to secure the implant in a loop around the bone portions,
wherein the fastening member includes at least one region configured to be severed in order to open the implant and access the sternum.

2. The implant of claim 1, wherein the at least one region configured to be severed has reduced mechanical strength.

3. The implant of claim 1, wherein the fastening member is coupled to the second end of the elongated member by a first injection molding process.

4. The implant of claim 3, wherein the engagement member is injection molded to the fastening member in a second injection molding process separate from the first injection molding process.

5. The implant of claim 3, wherein the at least one region configured to be severed is defined by a portion of the fastening member that remains exposed from the first injection molding process.

6. The implant of claim 1, wherein the at least one region configured to be severed includes a visual indicator that extends in a direction substantially perpendicular to an extension of the elongated member.

7. The implant of claim 1, wherein the at least one opening includes a first opening and a second opening and wherein the at least one region configured to be severed is located between the first opening and the second opening.

8. The implant of claim 7, wherein the first opening is configured to be located proximate to a first bone portion and the second opening is configured to be located proximate to a second bone portion to be fixed.

9. The implant of claim 1, wherein the at least one opening includes four openings, each of the openings being configured to receive a bone fastener.

10. The implant of claim 1, wherein the at least one opening includes eight openings, each of the openings being configured to receive a bone fastener.

11. An implant for bone fixation, comprising:
an elongated member configured to be wound around bone portions of a sternum of a patient that are to be fixed;
a fastening member coupled to the elongated member by injection molding, the fastening member including at least one opening for receiving a bone fastener; and
an engagement member coupled to the fastening member and configured to engage a portion of the elongated member so as to secure the implant in a loop around the bone portions,
wherein the fastening member includes at least one visual indicator having a region of reduced mechanical strength, the at least one visual indicator indicating a region of the fastening member to be severed in order to open the implant and access the sternum.

12. The implant of claim 11, wherein the engagement member is injection molded to the fastening member.

13. The implant of claim 11, wherein the elongated member comprises a plurality of engagement features provided along an extension of the elongated member, and wherein the engagement member is configured to be brought into selective engagement with one of the engagement features.

14. The implant of claim 11, further comprising a hook coupled to the elongated member.

15. The implant of claim 11, wherein the at least one opening of the fastening member comprises a locking feature configured to lock a bone fastener to the fastening member.

16. The implant of claim 15, wherein the locking feature includes a circumferential lip.

17. The implant of claim 16, further comprising a bone fastener including a thread configured to engage the circumferential lip.

18. The implant of claim 11, wherein the fastening member comprises a tapered portion surrounding the at least one opening, the tapered portion being configured to generate a compression force upon insertion of a bone fastener through the at least one opening.

19. The implant of claim 18, wherein the tapered portion is one of a conical taper or a spherical taper.

20. The implant of claim 11, wherein the fastening member comprises a metallic material and the elongated member comprises a polymeric material.

* * * * *